United States Patent [19]
Griffin, Jr. et al.

[11] Patent Number: 6,002,259
[45] Date of Patent: Dec. 14, 1999

[54] ELECTROSTATIC ADHESION TESTER FOR THIN FILM CONDUCTORS

[75] Inventors: Alfred J. Griffin, Jr., Dallas; Franz R. Brotzen, Houston; Daniel L. Callahan, Dallas, all of Tex.; Haining S. Yang, Boise, Id.

[73] Assignee: Rice University, Houston, Tex.

[21] Appl. No.: 09/008,969

[22] Filed: Jan. 20, 1998

[51] Int. Cl.⁶ .................................................. G01R 27/26
[52] U.S. Cl. ............................ 324/456; 324/662; 73/827
[58] Field of Search .............................. 73/827; 324/456, 324/452, 662, 71.5, 71.1

[56] References Cited

U.S. PATENT DOCUMENTS

| | | | |
|---|---|---|---|
| 5,245,293 | 9/1993 | Runner | 324/653 |
| 5,432,435 | 7/1995 | Strong | 324/705 |
| 5,624,625 | 4/1997 | Legressus | 324/456 |

OTHER PUBLICATIONS

English–language abstract for Russian patent No. SU 1805346 published Feb. 11, 1999 (1 sheet); Russian language original (3 sheets); and a certified English Translation (9 sheets).
English–language abstract for Russian patent No. SU 1627931 published Feb. 11, 1991 (1 sheet); Russian language original (3 sheets); and a certified English Translation (7 sheets).

International Search Report for PCT/US 98/06424 dated Feb. 18, 1999.

*Primary Examiner*—Josie Ballato
*Assistant Examiner*—Jose M. Solis
*Attorney, Agent, or Firm*—Conley, Rose & Tayon; Jeffrey C. Hood; Cyrus Bharucha

[57] ABSTRACT

A electrostatic adhesion tester for thin film conductors. In one embodiment, a device is provided for testing the adhesion strength of a thin film conductor that has been formed upon a substrate. The device includes an adhesion tester that is primarily comprised of a conducting portion. The conducting portion is applied to the thin film conductor so that it does not physically contact the thin film conductor, but leaves a small space there between. A power supply may further be provided for coupling to either the adhesion tester, the thin film conductor, or both in order to create a potential difference between the conducting portion and the thin film conductor. The potential difference creates an electric field between the conducting portion and the thin film conductor that induces stress in the thin film conductor. A measuring device may also be provided for coupling to the adhesion tester and the thin film conductor in order to measure an electrical parameter of the electric field, which is indicative of the adhesion strength.

36 Claims, 5 Drawing Sheets

| Materials | $\sigma_0$(MPa) | m |
|---|---|---|
| Pure Cu | 1.0 | 5.5 |
| Al-2% Cu | 1.6 | 3.3 |
| Al-SiO$_2$ Multilayer | 0.49 | 1.7 |

ELECTROSTATIC ADHESION TESTER FOR THIN FILM CONDUCTORS

FIELD OF THE INVENTION

The present invention relates to the field of adhesion testing and more particularly to a non-contact method for testing the adhesion of a thin film conductor and a variety of substrates.

DESCRIPTION OF RELATED ART

In the field of semiconductor fabrication, thin film metals are an important component in the fabrication of very large scale integration (VLSI) devices. These metal films are usually either deposited from a vapor phase or sputtered onto a substrate made of a different material. A typical application would be to deposit a thin film metal onto a dielectric layer to produce an interconnect level in a CMOS device.

VLSI fabrication requires that thin film metals must meet several strict structural, chemical, and electrical requirements. A universal concern in the fabrication of VLSI devices is the ability to etch submicron features into the thin film materials. To facilitate these miniature etchings, the fabrication of the materials must be carefully controlled. The demands for narrow line widths and high densities in the production of VLSI devices create a critical requirement for very low densities of particulate defects and film imperfections, such as pinholes. A result of these submicron etchings is that the underlying surface often becomes extremely rough. It is therefore necessary to have excellent adhesion between the underlying substrate and the overlaying thin film metal.

The adhesion of thin film metals used in VLSI processing must be of the highest quality throughout the time it is being deposited and continuing thereafter. If at any time, the metal film lifts from the substrate, the device will almost certainly fail. Therefore, excellent adhesion is necessary to ensure the reliability of the device. Adhesion strength will rapidly become a critical metric within the microelectronics industry, particularly as material systems and devices become more complex.

Various methods and techniques have been employed in the prior art to measure the adhesion strength of thin film metals on substrates. An early method of measuring adhesion involved pressing a piece of adhesive tape to the surface of the film and then pulling the tape off. The tape and substrate were then examined to determine if any or all of the film was pulled away. This method was called the "tape test," and failure of this test obviously implied that the film was not suitable for device fabrication. The most significant disadvantage of this test was that attempts at measuring the adhesive strength of the thin films were only qualitative and produced a wide distribution of results.

A second method that has been used in measuring adhesion strength is the "scratch" or "indentation method." This method produces results that depend both on the film hardness and on the adhesion quality of the thin film. To begin this process, pressure is applied, perpendicular to the film surface, to a chrome-steel point which is then moved horizontally across the film surface. The pressure on the point is increased until the point strips the film completely from the substrate. The groove from where the film was stripped is then observed with a microscope. The maximum pressure that was applied to the point is taken as a measure of the adhesion strength of the thin film. An improvement over the tape test, the indentation method is nevertheless very time consuming and requires that the adhesion strength be resolved from a combination of other measurements.

A third method previously used to measure the adhesion strength of thin film metals required a small pin to be epoxied to the surface of the film. Then the surrounding thin film material was removed from around the pin and epoxy. Next, a force was applied to the pin that was perpendicular to the surface of the thin film metal, until either the bond between the substrate and the thin film broke, or the epoxy bond between the thin film metal and the pin broke. This method often produced results that were inconsistent. The method also required a lengthy sample preparation and failed to produce any meaningful data if the epoxy bond broke first. Additionally, selection of an appropriate epoxy was critical to prevent any reaction with the thin film metal that may have skewed the results.

The above methods of testing the adhesion strength of thin film metals have proven to encompass the disadvantages of lengthy sample preparation times and producing only qualitative results where the strengths must be resolved from other measurements. It would thus be desirable to have an improved method of testing the adhesion strength of thin film metals.

SUMMARY OF THE INVENTION

The problems outlined above are in large part solved by an electrostatic adhesion tester for thin film conductors. In one embodiment, a device is provided for testing the adhesion strength of a thin film conductor that has been formed upon a substrate. The device includes an adhesion tester that is primarily comprised of a conducting portion. The conducting portion is applied to the thin film conductor so that it does not physically contact the thin film conductor, but leaves a small space there between. A power supply may further be provided for coupling to either the adhesion tester, the thin film conductor, or both in order to create a potential difference between the conducting portion and the thin film conductor. The potential difference creates an electric field between the conducting portion and the thin film conductor that induces stress in the thin film conductor. A measuring device may also be provided for coupling to the adhesion tester and the thin film conductor in order to measure an electrical parameter of the electric field, which is indicative of the adhesion strength.

The adhesion tester may further be configured to include one or more support portions that are connected to the conducting portion to accurately position the conducting portion in close proximity to the thin film conductor. The power supply mentioned above is adjustable in order to ramp up the potential difference between the conducting portion and the thin film conductor. Adjusting the potential difference controls the electric field between the conducting portion and the thin film conductor, and allows the electric field to be increased to the point where the thin film conductor peels away from the substrate and contacts the conducting portion. A measuring device may be connected to the thin film conductor and the conducting portion to detect the electrical parameter immediately before the thin film conductor contacts the conducting portion. Alternatively, the measuring device may be configured to detect the occurrence of a significant rate of change in the electrical parameter. Typically, both the adhesion tester and the substrate comprising thin film conductor are placed in a vacuum chamber in order to prevent arcing.

Still further, the present invention contemplates a method of testing the adhesion strength of a thin film conductor that is formed on a substrate. This method comprises the step of forming a capacitor by placing a conducting portion of an adhesion tester in close proximity to the thin film conductor without physically contacting the thin film conductor. A potential difference is then created between the conducting portion and the thin film conductor in order to create a corresponding electric field between the conducting portion and the thin film conductor. An electrical parameter of the capacitor is then measured, where the electrical parameter is indicative of the adhesion strength of the thin film conductor.

The present invention still further contemplates a system for testing the adhesion strength of a thin film conductor formed on a substrate. The system includes an adhesion tester, a power supply, and a measuring device. The adhesion tester includes a conducting portion adapted not to physically contact said thin film conductor when the adhesion tester is applied to said thin film conductor. The power supply is adapted for coupling to the adhesion tester or the thin film conductor and is capable of creating a potential difference between said conducting portion and said thin film conductor. The potential difference creates an electric field between the conducting portion and the thin film conductor. The electric field induces stress in the thin film conductor. The measuring device is adapted for coupling to the adhesion tester or the thin film conductor for measuring an electrical parameter of said electric field. The electrical parameter is indicative of said adhesion strength.

Similarly the present invention contemplates a method of testing the adhesion strength of a thin film conductor formed on a substrate, comprising the steps of forming a capacitor, creating a potential difference between a conducting portion of the capacitor and the thin film conductor, and measuring an electrical parameter of the capacitor indicative of the adhesion strength of the thin film conductor. Formation of the capacitor is achieved by placing a conducting portion of an adhesion tester in close proximity to said thin film conductor, wherein said conducting portion does not physically contact said thin film conductor. The potential difference creates an electric field between said conducting portion and said thin film conductor, wherein said electric field induces stress in said thin film conductor.

BRIEF DESCRIPTION OF THE DRAWINGS

Other objects and advantages of the invention will become apparent upon reading the following detailed description and upon reference to the accompanying drawings, in which.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Figure 1:
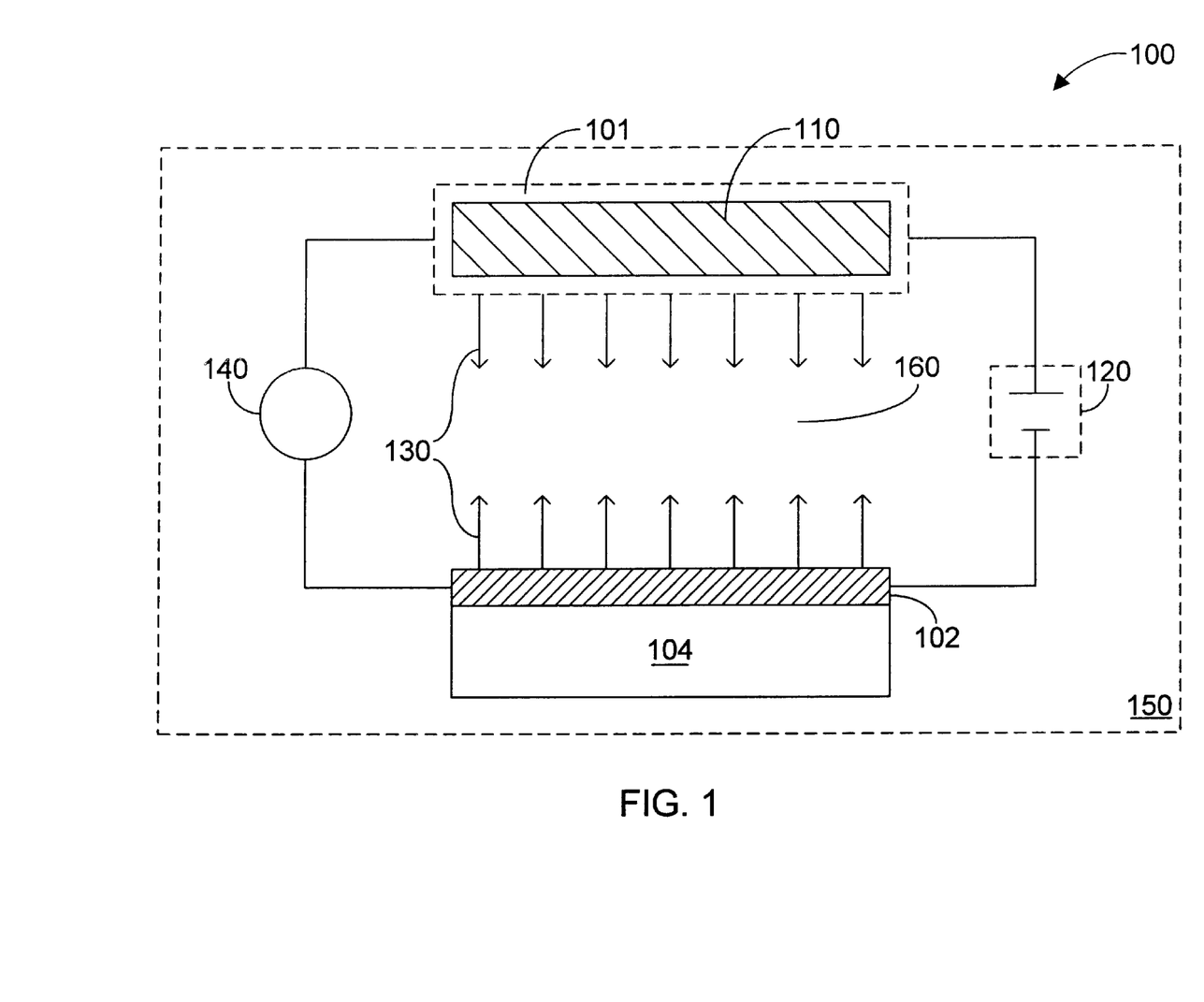
FIG. 1 is a diagram of electrostatic stresses between two parallel conductor plates.

Referring now to FIG. 1, a schematic diagram of the electrostatic stresses between two parallel conductor plates in accordance with one embodiment of the present invention is shown. The principle of this technique is the use of a quantifiable normal tensile force generated by an electrostatic field to delaminate thin film metallizations from their semiconductor substrates. FIG. 1 shows a system 100 for testing the adhesion strength of a thin film metal 102 that is formed on a substrate 104. The thin film metal 102 is coupled to the conducting portion 110 of an adhesion tester 101 by a power supply 120. Power supply 120 is preferably adjustable, and adapted to create a positive charge on the conducting portion 110. The thin film metal 102 may be either negatively charged or grounded. The model for this system is the simple parallel plate capacitor. For a conducting portion 110 with a uniform surface charge density $\rho$ facing a thin film metal 102, which is grounded, according to Gauss's law one can calculate the electric field 160 in the intervening medium as being equal to the surface charge density divided by the product of the permittivity of vacuum and the dielectric constant of the material separating the conducting portion 110 and the thin film metal 102. The dielectric separating the conducting portion and the thin film metal in this particular embodiment is air, which has a relative permittivity of 1.00059. The electric field 160 may further be defined as the resultant electrostatic force per unit positive charge. The electrostatic forces 130 generated on the surfaces of the conducting portion 110 and the thin film metal 102 are normal to the surfaces, hence, the electric field 160 can be represented in a scalar relationship $E=F/q$. Considering the charge density $\rho=q/A$ and the mechanical stress $\sigma=F/A$, the electrostatic field 130 can be further expressed as $E=\sigma/\rho$. The relationship between the mechanical stress $\sigma$ and field E can be represented as $\sigma=\kappa\epsilon_0 E^2$.

The electric field 160 in the special case of parallel plate geometry can be simply expressed as the potential or applied voltage V, divided by the plate separation distance, d. Generally speaking, for the case of adhesion testing, the medium is a vacuum which has a permittivity of $\epsilon_0=8.85\times 10^{-12} C^2/Nm^2$. Hence, the electrostatic stress 130 can be expressed in terms of only an applied voltage and a separation distance as $\sigma(MPa)=8.85[(V(kV))/(d(\mu m))]^2$.

It should be noted that the preceding discussion applies not only for metal films deposited on a substrate, but also for other thin conductive films as well. In particular, the adhesion strength of a dielectric film can also be tested using the invention if the dielectric material is exposed to an electric field that causes it to undergo dielectric breakdown. Under this condition, the dielectric film becomes conductive, and the above expression for electrostatic stress can be used to determine the electrostatic stress on the dielectric film.

The feasibility of this technique relies on attaining adequately high values of E and, hence, $\sigma$. To generate stresses of up to 100 Mpa in the metallizations, the electric field 160 should preferably be on the order of approximately $10^9$ V/m. The measuring device 140 is used to measure an electrical parameter of the electric field 160. The simplest measurement to record is the potential difference between the conducting portion 110 and the thin film metal 102.

To generate a stress as high as 100 Mpa using a power supply with a maximum output of about 10 kV, the separation distance between the conducting portion 110 and the thin film metal 102 should preferably be on the order of microns. Hence, it is typically more practical to control the electric field by adjusting the relatively large voltage rather than the relatively small gap.

Figure 2:
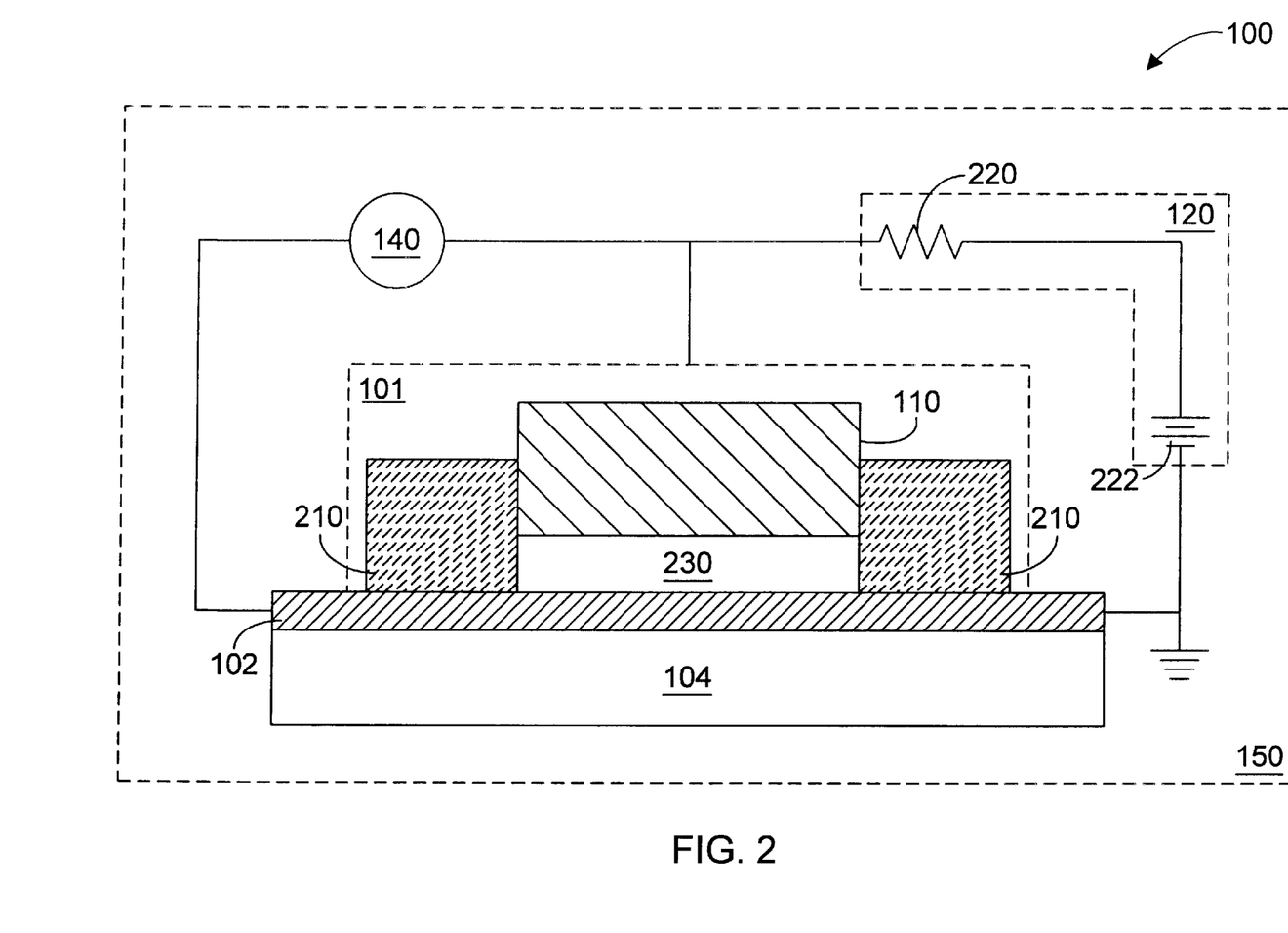
FIG. 2 is a schematic diagram of an electrostatic adhesion tester.

FIG. 2 is a schematic diagram of an embodiment of an electrostatic adhesion test system 100. Test system 100 includes an adhesion test 101, a power supply 120, and a measuring device 140. Adhesion tester 101 includes two ceramic supports 210 connected to the conducting portion 110. The conducting portion 110 is typically comprised of copper and is approximately 0.65 mm thick in one embodiment. The adhesion tester 101, consisting of the two ceramic supports 210 and the copper conducting portion 110 there between, is applied to the thin film metal 102 such that the ceramic supports 210 are in contact with thin film metal 102.

In one presently preferred embodiment, the contact surfaces of the ceramic supports 210 are comprised of finely polished μm alumina. Ceramic supports 210 hold the conducting portion 110 in such a way as to prevent conducting portion 110 from contacting thin film metal 102. The conducting portion 110 is held in close proximity to thin film metal 102, creating a gap between the two of approximately 2 μm. This gap may suitably be filled with a variety of dielectrics including air. Suitable dimensions of ceramic supports 210 and the copper conducting portion are approximately 7×10×8 mm.

An alternate method (not shown) of applying conducting portion 110 to thin film metal 102 is to connect conducting portion 110 to a mechanical arm that positions the surface of the conducting portion 110 parallel to the surface of the thin film metal 102. The mechanical arm could thereby leave a small gap of approximately 2 μm between the two surfaces without the need of any support portions, such as those shown in FIG. 2.

To prevent arcing, the device is placed in a vacuum chamber 150. In one embodiment, a diffusion pump backed up by a mechanical pump provides a vacuum of $10^{-6}$ torr, which is adequate for the proper operation of the device. A cold trap may be used to diminish oil contamination of the sample. Also, the edges of the copper conducting portion 110 may be gently rounded to further prevent arcing.

The potential difference between the conducting portion 110 and the thin film metal 102 may be provided by applying a voltage from a power supply 120. In the preferred embodiment, power supply 120 includes a voltage source 222 in series with a resistor 220. An exemplary power supply is a Sorensen-5 voltage source, whose maximum voltage is 12 kV at a current of 50 mA. The measuring device 140 is intended to measure an electrical parameter of the electric field between the conducting portion 110 and the thin film metal 102. For example, measuring device 140 could measure the capacitance or the potential difference between the two surfaces. The simplest measurement to record is the potential difference or voltage. An exemplary device to measure the exact applied voltage from the power supply 120 is a BK Precision multimeter (Model: 2835 DMM). The resistor 220 used in this invention is typically a 50 Ω resistor. In testing a specimen, the electric field is raised gradually by increasing the voltage until a short is noticed. This is the point at which the thin film metal 102 contacts the conducting portion 110. The voltage at failure is read on the voltmeter and used to determine the delamination stress of the thin film metal 110.

Between sets of experiments, the adhesion tester 101 is cleaned and polished to prevent particle accumulation. Changes in the gap between the conducting portion 110 and the thin film metal 102 are measured by scanning electron microscopy and incorporated into the necessary calculations. Generally speaking, gaps from 1.2 to 4 μm are utilized.

Figure 3:
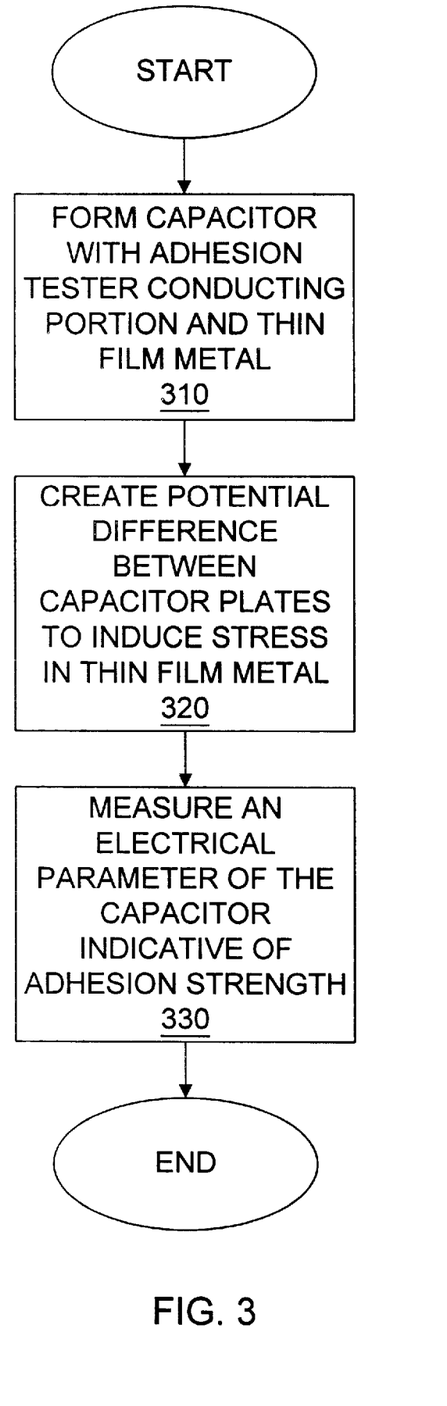
FIG. 3 is a flow diagram of a method of testing an adhesion strength.

In FIG. 3, a flow diagram for one embodiment of a method for testing the adhesion strength of a thin film metal is disclosed. Initially, a capacitor is formed as indicated by reference numeral 310. The formation of the capacitor is accomplished by placing a conducting portion of the adhesion tester in close proximity to the thin film metal without contacting the conducting portion to the thin film metal. In a presently preferred embodiment, a gap between the conducting portion and the thin film metal is suitably in the range of approximately 1 to 4 microns. After the capacitor has been formed, a potential difference between the plates of the capacitor is created as indicated in reference numeral 320 of FIG. 3. The potential difference between the plates of the capacitor creates an electrical field that induces stress in the thin film metal. After the potential difference has been created, an electrical parameter of the capacitor is measured. The electrical parameter chosen for measurement is indicative of the adhesion strength of the thin film metal. The measurement of the electrical parameter is indicated in FIG. 3 by reference numeral 330. In one embodiment, the adhesion tester includes one or more support structures coupled to the conducting portion to facilitate placing the conducting portion in close proximity to the thin film metal without touching the thin film metal. In one embodiment, the method further includes the step (not shown in FIG. 3) of adjusting the potential difference between the conducting portion and the thin film metal during the measuring. In this manner, the electrical field between the conducting portion and the thin film metal may be controlled during the measurement portion of the method. In one embodiment, the adjusting involves increasing the potential difference until the thin film metal contacts the conducting portion of the adhesion tester. In this embodiment, the measuring preferably determines a value of the electrical parameter immediately prior to a point when the thin film metal contacts the conductive portion. It is contemplated in this embodiment that the increasing electrical field caused by the increasing potential difference ultimately induces enough stress in the thin film metal to displace the thin film metal from the underlying substrate and, ultimately, forces the thin film metal into contact with the conducting portion of the adhesion tester. In one embodiment, it is contemplated that the potential difference between the conducting portion and the thin film metal results in a first rate of change in the electrical parameter during a first duration. During a second duration, the measuring detects a second rate of change typically greater than the first rate of change. In this embodiment, the measuring determines the value of the electrical parameter immediately after the first duration. In this embodiment, it is contemplated that, prior to the point at which the thin film metal delaminates, a rate of change in the measured electrical parameter whether it be potential difference, capacitance, capacitor current, or some other appropriate parameter, will be significantly different than the rate of change of the particular parameter after the delamination of the metal and, more particularly, after the point at which the thin film metal contacts the conducting portion of the adhesion tester. It is contemplated that one embodiment of the present invention may be designed to measure the rate of change of a desired electrical parameter rather than measuring and reporting the electrical parameter directly.

In one embodiment, creating the potential difference is accomplished by applying a voltage to the conducting portion, the thin film metal, or both. The voltage creates an electric field between the conducting portion and the thin film metal that induces a stress in the thin film metal. The creation of the potential difference is preferably accomplished in a presently preferred embodiment by connecting a power supply across the thin film metal and the conducting portion of the adhesion tester. In a preferred embodiment, the adhesion tester and the substrate are placed in a vacuum chamber prior to performing the adhesion test to prevent arcing. In one embodiment, the electrical parameter is measured at a predetermined time interval after the potential difference is created. In this embodiment, it is envisioned that a pass fail test may be performed by simply measuring an electrical parameter at a specified time interval and, if the measured parameter is within specification, the thin film is designated to have adequate adhesion to the substrate. In alternative embodiments, the electrical parameter may be the potential difference between the conducting portion and the thin film metal or a capacitance of the capacitor comprising the conducting portion and the thin film metal. In a presently preferred embodiment, the potential difference is in the range of approximately 1 kV to 12 kV.

Figure 4:
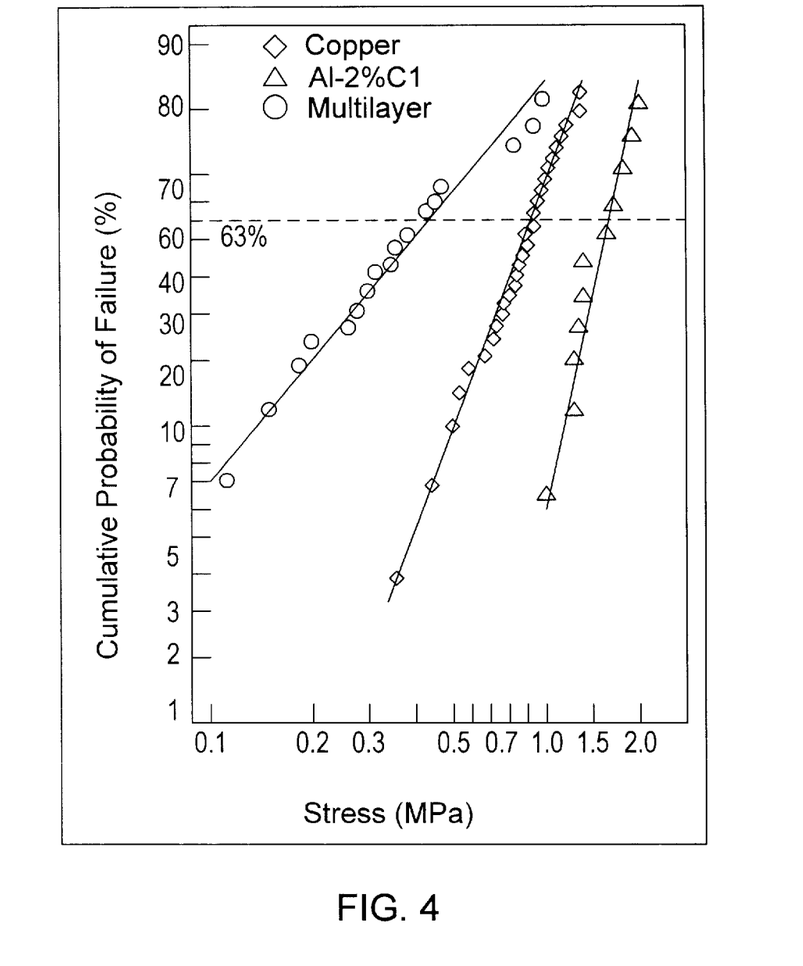
FIG. 4 is a graph of the Weibull distribution of adhesion strengths from three metallizations.

FIG. 4 is a plot of the Weibull distribution of adhesion strengths from the following metallizations: aluminum-copper (2%) alloy, unalloyed copper, and an aluminum silica multilayer. The three metallizations were 1 $\mu$m thick and had been dc magnetron sputtered onto a partially oxidized single-crystal silicon substrate. The electrostatic adhesion test system typically measures adhesion strengths that exhibit considerable scatter and should consequently be subjected to Weibull statistical analysis.

Taking the natural logs of the Weibull distribution function ($\sigma_0$=0) twice gives $\ln \ln[1/(1-P_f(V))]=m \ln (\sigma/\sigma_0)$ with $\sigma_0$ being the characteristic stress defined as the stress at which 63% of the population has failed. In the previous equation, m is the Weibull modulus indicative of flaw-sensitivity. Thus a plot of the left-hand side of the equation against $\ln(\sigma)$ is a straight line. The slope of the line is m and the x -intercept is $\ln(\sigma_0)$. The Weibull plots in FIG. 3 point to a linear relationship, indicating that the Weibull statistics can be applied to the adhesion strengths analysis.

Figure 5:
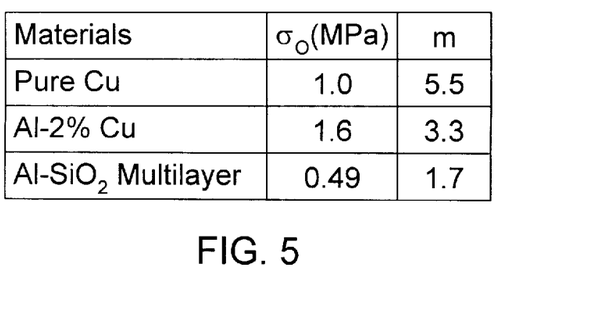
FIG. 5 is a table of the characteristic strengths and Weibull modulus of the tested films.

FIG. 5 lists the characteristic strength, $\sigma_0$, and the Weibull modulus, m, for each of the metallizations. It is seen from this figure that the Al-Cu(2%) alloy metallization has a higher characteristic adhesion strength than the other two metallizations. The Al multilayer film has the lowest characteristic strength. At the same time, the Weibull modulus of the Al-Cu(2%) metallization is larger than those of copper and of the Al-multilayer. Thus, there is less scattering of the delamination stress in the Al-Cu(2%) metallization than that in the other two metallizations.

Figure 6A:
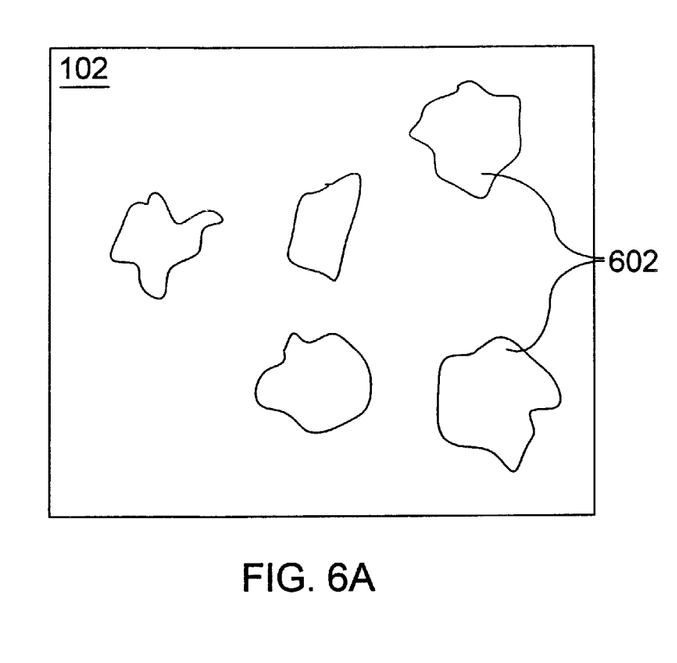
FIG. 6A is a top view of micro-blister adhesion failure.
Figure 6B:
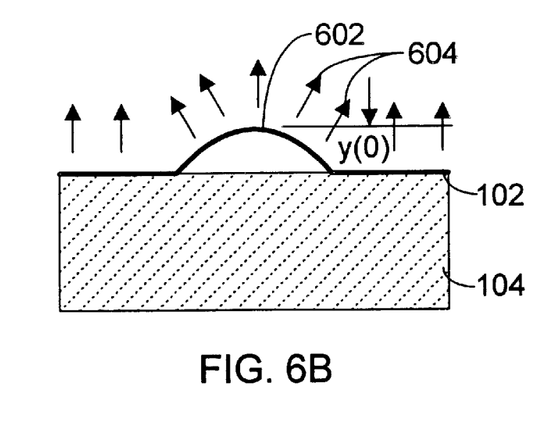
FIG. 6B is a cross section of one of the micro-blisters in 3A.

FIGS. 6A and 6B illustrate the delamination of a thin film metal 102 as it occurs through blister formation. The blister 602 may be viewed with the use of a field-emission scanning electron microscope (FE-SEM). The size of the blisters 602 are typically about 15 $\mu$m in diameter. The electrostatic forces 604 cause the central part of the blister 602 to rupture, and thus make contact with the conducting portion 110 of the adhesion tester 101. FIG. 6B also shows the blister 602 growing under the electrostatic field.

The delamination and rupture of a thin film metal 102 occurs as a result of the electrostatic field gradually increasing. This increase in the electrostatic field causes the normal stress to lift the film 102 from its substrate 104 at an interfacial flaw, which provides a potential delamination site. When the critical delamination stress is reached, a region at the flaw is detached forming a blister 602. The blister 602 will grow spontaneously, without the need of a field stress greater than the critical delamination stress. The meridional tensile stresses in the film will also rise. When these stresses reach the fracture strength of the film 102, parts of the film 102 are delaminated and touch the conducting portion 110 of the adhesion tester 101, thus creating a short.

The delamination flaws at the interface could be voids, interface contaminations, grain boundaries, or interfacial chemical reactants. If more than two kinds of flaws were active in initiating fractures, the measured data would fall on a non-linear relationship in the Weibull plots. A "knee" would appear between linear portions of the graph with different slopes. However, all of the plots in FIG. 4 show a clearly linear relationship.

For the blisters 602 shown in FIGS. 6A and 6B, the stresses reach a maximum at the center of the blister. For a typical aluminum film blister, the tensile stress is calculated to be approximately 83 MPa. This stress is higher than the rupture strength of 55 MPa, which is measured from blister testing of free standing Al(1%)Si film of the same thickness. For comparison, the ultimate tensile strength of bulk aluminum (1100) is 89 MPa. The thin film metal 102 is ruptured when the tensile stress at the center of the blister 602 reaches the fracture strength of the material. The ruptured film then creates a short by touching the conducting portion 110 of the adhesion tester 101.

The lower limit of the central height of a typical blister 602 is 0.34 $\mu$m. Likewise, the upper limit of the central height of a typical blister 602 is 1 $\mu$m. Because the blister growth in adhesion testing is a much faster process than that in a bulge test, the fracture strain is expected to be smaller than that in a bulge test and, hence, the central height of a blister will be smaller than the calculated value.

As mentioned above, measuring the potential difference between the conducting portion 110 and the thin film metal 102 is the preferred method of determining the adhesion strength of the thin film metal 102. However, alternate methods may be used. One of the alternate methods is to use measuring device 140 to determine when the electric field between the conducting portion 110 and the thin film metal 102 undergoes a significant rate of change. The increase in the rate of change of the electric field is easily detected because the time from when the thin film metal 102 first begins to blister to the point where it expands and contacts the conducting portion 110 is extremely short and in the order of micro seconds. This is much different from the slow and predictable rate of change that results from the power supply being steadily ramped up to the point where the short circuit is noticed. Therefore, it is quite easy to differentiate between the two rates of change and the measuring device could be designed accordingly.

Another alternate method of determining the adhesion strength between the thin film metal 102 and the substrate 104 is to create a pre-determined potential difference between the conducting portion 110 and the thin film metal 102 for a pre-determined period of time, and then visually inspect the sample to determine if any delamination in the form of blistering occurred. In other words, if the sample is subjected to a pre-determined level of stress from an electric field, and no delamination occurs, then the adhesion strength could be considered adequate, having passed a threshold test.

It will be appreciated by those skilled in the art that the present invention and the preferred embodiment of the invention described herein are useful in obtaining quantitative information regarding the adhesion strengths of thin film metals. Various modifications and changes may be made to each and every element of the methods and apparatus described as would be obvious to a person skilled in the art having the benefit of this disclosure. It is intended that the following claims be interpreted to embrace all such modifications and changes and, accordingly, the specification and drawings are to be regarded in an illustrative rather than a restrictive sense.

We claim:

1. A method of testing the adhesion strength of a thin film conductor formed on a substrate, comprising the steps of:
   forming a capacitor by placing a conducting portion of an adhesion tester in close proximity to said thin film conductor, wherein said conducting portion does not physically contact said thin film conductor;
   creating a potential difference between said conducting portion and said thin film conductor, wherein said potential difference creates an electric field between said conducting portion and said thin film conductor, wherein said electric field induces stress in said thin film conductor; and
   measuring an electrical parameter of said capacitor, wherein said electrical parameter is indicative of said adhesion strength.

2. The method of claim 1, wherein said adhesion tester further comprises one or more support portions coupled to said conducting portion, wherein said placing said conducting portion comprises applying said adhesion tester to said thin film conductor wherein said one or more support portions contact said thin film conductor.

3. The method of claim 1, further comprising:
   adjusting said potential difference between said conducting portion and said thin film conductor during said measuring, to control said electric field created between said conducting portion and said thin film conductor.

4. The method of claim 3, wherein said adjusting said potential difference between said conducting portion and said thin film conductor comprises increasing said potential difference until said thin film conductor contacts said conducting portion.

5. The method of claim 4, wherein said measuring determines a value of said electrical parameter immediately prior to a point where said thin film conductor contacts said conducting portion.

6. The method of claim 3, wherein said adjusting said potential difference between said conducting portion and said thin film conductor results in a first rate of change in said electrical parameter during a first duration;
   and further wherein said measuring detects a second rate of change during a second duration, wherein said second rate of change is greater than said first rate of change; and
   further wherein said measuring further determines said electrical parameter immediately after the first duration.

7. The method of claim 1, wherein said creating a potential difference comprises applying a voltage to at least one of said conducting portion and said thin film conductor, wherein said voltage creates an electric field between said conducting portion and said thin film conductor, wherein said electric field induces stress in said thin film conductor.

8. The method of claim 7, wherein said creating a potential difference between said conducting portion and said thin film conductor comprises connecting a power supply to said conducting portion and to said thin film conductor.

9. The method of claim 1, further comprising:
   placing said substrate in a vacuum chamber;
   wherein said steps of placing an adhesion tester, creating a potential difference, and measuring said electrical parameter are performed in said vacuum chamber to prevent arcing.

10. The method of claim 1, wherein said electric field induces thin film conductor delamination, wherein said measuring an electrical parameter is performed at a pre-determined time interval after said creating.

11. The method of claim 1, wherein said electrical parameter is a potential difference between said conducting portion and said thin film conductor.

12. The method of claim 1, wherein said electrical parameter is a capacitance between said conducting portion and said thin film conductor.

13. The method of claim 1, wherein said measuring comprises measuring a rate of change of said electrical parameter.

14. The method of claim 1, wherein, after said applying, said conducting portion and said thin film conductor are separated by a dielectric.

15. The method of claim 14, wherein said dielectric is air.

16. The method of claim 1 wherein said potential difference is in the range of 1 kV to 12 kV.

17. The method of claim 1 wherein, after said applying, said first and second plates are separated by a distance ranging from 1.2 to 4 micrometers.

18. A method of testing the adhesion strength of a thin film conductor formed on a substrate, comprising the steps of:
   forming a capacitor by placing a conducting portion of an adhesion tester in close proximity to said thin film conductor, wherein said conducting portion does not physically contact said thin film conductor;
   creating a potential difference between said conducting portion and said thin film conductor, wherein said potential difference creates an electric field between said conducting portion and said thin film conductor, wherein said electric field induces stress in said thin film conductor; and
   determining a condition of said thin film conductor after said creating, wherein said condition of said thin film conductor is indicative of said adhesion strength.

19. The method of claim 18, wherein said creating said potential difference comprises applying said potential difference for a pre-determined period of time.

20. A method of testing the adhesion strength of a thin film conductor formed on a substrate, comprising the steps of:
   applying an adhesion tester to said thin film conductor, wherein said adhesion tester comprises a conducting portion coupled to one or more support portions, wherein said one or more support portions contact said thin film conductor, wherein said conducting portion does not physically contact said thin film conductor;
   creating a potential difference between said conducting portion and said thin film conductor, wherein said potential difference creates an electric field between said conducting portion and said thin film conductor, wherein said electric field induces stress in said thin film conductor; and
   measuring an electrical parameter of said electric field, wherein said electrical parameter is indicative of said adhesion strength.

21. A system for testing the adhesion strength of a thin film conductor, wherein said thin film conductor is formed on a substrate, the system comprising:

an adhesion tester comprising a conducting portion, wherein said conducting portion is adapted to not physically contact said thin film conductor when said adhesion tester is applied to said thin film conductor;

a power supply adapted for coupling to at least one of said adhesion tester and said thin film conductor for creating a potential difference between said conducting portion and said thin film conductor, wherein said potential difference creates an electric field between said conducting portion and said thin film conductor, wherein said electric field induces stress in said thin film conductor; and a measuring device adapted for coupling to at least one of said adhesion tester and said thin film conductor for measuring an electrical parameter of said electric field, wherein said electrical parameter is indicative of said adhesion strength.

22. The system of claim 21, wherein said adhesion tester further comprises one or more support portions coupled to said conducting portion, wherein said one or more support portions contact said thin film conductor formed on said substrate when said adhesion tester is applied to said thin film conductor.

23. The system of claim 21, wherein said power supply is adjustable.

24. The system of claim 23, wherein said power supply is operable to increase said potential difference between said conducting portion and said thin film conductor until said thin film conductor contacts said conducting portion; and wherein said measuring device detects said electrical parameter immediately prior to when said thin film conductor contacts said conducting portion.

25. The system of claim 23, wherein said power supply is operable to adjust said potential difference between said conducting portion and said thin film conductor to produce a first rate of change in said electrical parameter during a first duration;

and further wherein said measuring device detects a second rate of change during a second duration, wherein said second rate of change is greater than said first rate of change; and further wherein said measuring device is configured to determine said electrical parameter immediately prior to occurrence of said second rate of change.

26. The system of claim 21, wherein said conducting portion operates as a first plate of a capacitor, wherein said thin film conductor operates as a second plate of said capacitor;

wherein said power supply operates to create a potential difference between said first and second plates of said capacitor, wherein said potential difference creates an electric field between said first and second plates; and wherein said measuring operates to measure an electrical parameter of said capacitor, wherein said electrical parameter is indicative of said adhesion strength.

27. The system of claim 21, wherein said power supply is operable to apply a voltage to at least one of said conducting portion and said thin film conductor, wherein said voltage creates an electric field between said conducting portion and said thin film conductor, wherein said electric field induces stress in said thin film conductor.

28. The system of claim 21, further comprising:

a vacuum chamber configured to receive said substrate;

wherein said adhesion tester is positioned in said vacuum chamber when said adhesion tester is applied to said thin film conductor; and wherein said measuring device operates to measure said electrical parameter of said electric field in said vacuum chamber in order to prevent arcing.

29. The system of claim 21, wherein said electric field induces thin film conductor delamination, wherein said measuring device operates to measure said electrical parameter at a time after said potential difference creates said electric field.

30. The system of claim 21, wherein said electrical parameter is a potential difference between said conducting portion and said thin film conductor.

31. The system of claim 21, wherein said electrical parameter is a capacitance between said conducting portion and said thin film conductor.

32. The system of claim 21, wherein said measuring device measures a rate of change of said electrical parameter.

33. The system of claim 21, further comprising:

a dielectric positioned between said conducting portion and said thin film conductor.

34. The system of claim 33, wherein said dielectric is air.

35. The system of claim 21 wherein said potential difference is in the range of 1 kV to 12 kV.

36. A system for testing the adhesion strength of a thin film conductor, wherein said thin film conductor is formed on a substrate, the system comprising:

an adhesion tester, comprising:
one or more support portions;
a conducting portion connected to said one or more support portions;
wherein said one or more support portions are adapted to contact said thin film conductor when said adhesion tester is applied to said thin film conductor,
wherein said conducting portion is adapted to not physically contact said thin film conductor when said adhesion tester is applied to said thin film conductor,
wherein, when said adhesion tester is applied to said thin film conductor, said conducting portion operates as a first plate of a capacitor and said thin film conductor operates as a second plate of said capacitor;

a power supply adapted for coupling to said adhesion tester and said thin film conductor for creating a potential difference between said first and second plates of said capacitor, wherein said potential difference creates an electric field between said first and second plates, wherein said electric field induces stress in said thin film conductor; and a measuring device adapted for coupling to at least one of said adhesion tester and said thin film conductor for measuring an electrical parameter of said capacitor, wherein said electrical parameter is indicative of said adhesion strength.

* * * * *